United States Patent [19]

Wegfahrt et al.

[11] 4,108,974

[45] Aug. 22, 1978

[54] RADIOIMMUNOASSAY FOR THYROID HORMONE

[75] Inventors: Paul F. Wegfahrt, Oakland; Nathan Lewin, Corte Madera; James F. Monthony, Albany, all of Calif.

[73] Assignee: Bio-Rad Laboratories, Inc., Richmond, Calif.

[21] Appl. No.: 718,308

[22] Filed: Aug. 27, 1976

[51] Int. Cl.² ............................................. G01N 33/16
[52] U.S. Cl. .................................... 424/1; 23/230 B; 23/230.6; 424/12; 252/408
[58] Field of Search .................... 260/6, 7.6, 8; 424/1, 424/12, 1.5; 23/230 B, 230.6; 252/408

[56] References Cited

U.S. PATENT DOCUMENTS

| | | | |
|---|---|---|---|
| 3,514,429 | 5/1970 | Stahmann et al. | 424/12 |
| 3,555,143 | 6/1967 | Axen | 424/1 |
| 3,716,632 | 2/1973 | Fader et al. | 424/1 |
| 3,853,987 | 12/1974 | Dreyer | 424/1 |
| 3,911,096 | 10/1975 | Chopra | 424/1 |
| 3,941,564 | 3/1976 | Fader et al. | 23/230 B |
| 3,959,079 | 5/1976 | Mareschi et al. | 260/112 R |
| 3,983,001 | 9/1976 | Coupek et al. | 260/112 R X |
| 3,985,617 | 10/1976 | Yugari et al. | 260/112 R X |
| 3,985,867 | 10/1976 | Redshaw | 424/1.5 |

*Primary Examiner*—Benjamin R. Padgett
*Assistant Examiner*—Christine M. Nucker
*Attorney, Agent, or Firm*—Townsend and Townsend

[57] ABSTRACT

The method of this invention is characterized by the use of hydrolyzed cross-linked polyacrylamide particles to which have been bonded, by means of covalent bonds, antibodies against the thyroid hormone to be determined. The particles selected are of a size which forms a stable hydrophyllic suspension. In the preferred embodiment a measured quantity of unextracted human serum is mixed together with a blocking agent in an amount sufficient to displace the thyroid hormone to be measured from thyroxine binding globulin (TBG), a radioactively labeled thyroid hormone of the type to be measured, and the antibody-polyacrylamide complex. The hormone to be measured is displaced by the blocking agent followed by the competitive binding of the labeled and unlabeled hormone to the antibody-polyacrylamide particles. The particles are readily separated from the sample liquid and the radioactivity of the particle material and/or in the liquid is determined. Particles containing Alcian yellow or blue dye facilitate practice of the method.

19 Claims, 1 Drawing Figure

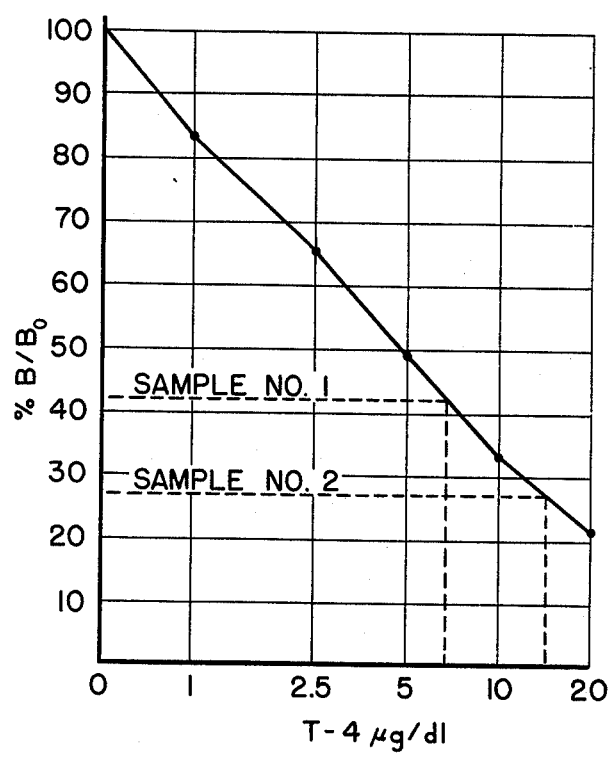
FIG._1.

RADIOIMMUNOASSAY FOR THYROID HORMONE

BACKGROUND OF THE INVENTION

This invention relates to a method for the radioimmunoassay for thyroid hormones and to reagents for use in such an assay.

PRIOR ART

The covalent bonding of antibodies to water insoluble polymers is taught in U.S. Pat. No. 3,555,143 to Axen et al.. The antibodies are covalently bonded to the polymers and are then used in assays for proteins and polypeptides. Crosslinked dextran is the polymer used in the preferred embodiment.

Corning IMMO PHASE, a commercial radioimmunoassay system for T-4 makes use of antibodies covalently bound to porous glass particles which are then suspended in phosphate buffered saline containing bovine serum albumins and thimerosal for blocking thyroxin binding globulin (TBG).

The commercialized radioimmunoassay by Sorin utilizes a double antibody technique in which the second antibody is immobilized on cellulose. The assay itself is for a different hormone, namely thyroid stimulating hormone.

Copending patent application Ser. No. 621,197 filed Oct. 9, 1975 by Monthony et al. is directed to a solid phase immunofluorescent assay in which immune reactants are covalently bound to water insoluble hydrophyllic polymeric particles including polyacrylamide particles as used in the present invention.

U.S. Pat. No. 3,911,096 to Chopra discloses the use of blocking agents for displacing thyroid hormone from unextracted serum preparatory to determining the thyroid hormone in a competitive binding procedure.

SUMMARY OF THE INVENTION

The present assay method is based on the principles of radioimmunoassay described by Berson and Yalow.[1] In the test procedure of the preferred embodiment a measured amount of patient serum or thyroxine standard is mixed with radioactively labeled thyroxine (T-4$^{125}$I) and 8-anilino-1-napthalene sulphonic acid (ANS) followed by the addition of an immobilized T-4 antiserum (T-4 antiserum covalently bound to aqueous suspendable hydrolyzed polyacrylamide beads). The mixture is allowed to incubate at room temperature. The ANS displaces the thyroxine from the serum proteins. During incubation the displaced thyroxine competes with the labeled thyroxine for the immobilized throxine antiboides on the basis of their relative concentrations.

[1] Berson, S. A. and Yalow, R. S., J. Clin. Invest., 39, 1157 (1960).

The quantity of labeled throxine that binds with the antibody is inversely related to the amount of unlabeled endogenous thyroxine present in the serum. After incubation the mixture is centrifuged and the immobilized thyroxine-antibody complex is concentrated at the bottom of the tube in the form of a pellet. The unbound thyroxine in the supernatant is decanted and the radioactivity associated with the pellet is counted. A standard curve is prepared using precalibrated thyroxine standards in a human serum base. The concentration of thyroxine in the patient serum is determined from the standard curve.

A unique reagent is also provided by this invention for use in the immunoassay which comprises hydrolyzed cross-linked polyacrylamide particles having absorbed thereon at least one dye selected from Alcian yellow and Alcian blue. These dyed particles have significant practical advantages for the laboratory technician performing the assay. Considering that the polyacrylamide particles are water white and difficult to see, the dyed particles make it easier to monitor the initial filling operations of the various vessels employed. Following the centrifugation step in which the pellet is formed the dye permits easy location of the pellet for the remaining manipulative steps. The dye also helps the technician avoid inadvertently decanting beads with the supernatant following the centrifugation step. The dyes utilized in this reagent have been found to be unique in that they have demonstrated the ability to be surface absorbed on the polyacrylamide particles and to remain thereon in the ionic buffer environment which exists during the various steps of the assay procedure.

The overall assay procedure itself has a number of unique characteristics. The hydrolyzed cross-linked polyacrylamide particles employed herein as solid phase substrates for the antibodies are characterized by their ability to form stable hydrophyllic suspensions. As a result the reaction mixture, during which thyroid hormone is separated from serum proteins and competitive binding in the presense of radioactive tracer with the antibody occurs, requires no agitation to maintain the desired homogeneous condition. The method contemplates accelerating the incubation step by application of heat, for example, incubation at temperatures of about 37° – 50° C. This heating is readily accomplished with the present method because agitation is not required. Prior art procedures such as that of Axen et al (dextran particles), Sorin (cellulose particles) and Corning (glass particles) are distinguished in that such types of particles settle out relatively rapidly and the assays require continuous stirring of the immobilized reagents during addition and constant agitation of the solution throughout the incubation period. Where heating is employed the constant agitation is a most inconvenient operation. For completeness it should be stated that the Corning procedure utilizing glass particles for immobilization of the antibody perhaps has less of a settling problem than the others in short assays. Overall, however, the settling problem still exists. This is apparent from the fact that the commercially offered materials are provided in factory pre-filled tubes for each assay sample indicating the difficulty of obtaining uniform suspensions for precise aliquot sampling.

Other unique aspects of the present invention stem from the low non-specific binding properties of the polyacrylamide particles. Non-specific binding is so low that the initially separated solid phase particles following incubation can be directly measured for radioactivity levels in the absence of any initial washings. Prior art solid phase supports such as that of the above referenced Axen et al. patent require preliminary washing steps prior to the measurement of the radioactive tracer. Elimination of the washing steps as well as eliminating the addition of other elements such as surfactants as used by Axen et al. to reduce non-specific absorption provides a substantial increase in the speed and the convenience of the present assay procedure.

The foregoing advantages are obtained through the use of hydrolyzed cross-linked polyacrylamide particles which in the unhydrolyzed form have a particle size of 0.1 – 10 microns, usually about 1 – 5 microns, and preferably having a particle size distribution centered about 5 microns. Reference is made to the above identified Monthony et al. patent application for other information as to such particles in connection with immune reactants and the prior art relevant thereto.

DESCRIPTION OF THE PREFERRED EMBODIMENT

Manufacture of Antibody - Beads

Polyacrylamide beads (1 - 5 microns) obtained from Bio-Rad Laboratories, Inc. of Richmond, California under the trademark "BIO-GEL P" are hydrolyzed with strong alkali to obtain the carboxyllic acid form. As a result of this process the hydrated beads swell considerably (5-10 $\mu$) due to ionic repulsions and reduction of cross linking. Such beads have a density very near to that of water and aqueous suspensions of them are quite stable. Continuous mixing is not necessary and near homogeneity is maintained over periods of hours.

Antibodies are covalently linked to the hydrolyzed beads via the formation of amide bonds, which link the carboxylate groups of the bead to free amine groups on the antibody. This can be accomplished by treating a suspension of the hydrolyzed beads with a coupling agent such as a water soluble carbodiimide followed by addition of a dilute solution of whole antiserum or purified antibodies, and the resulting mixture allowed to stand.

The antibody-bead complex may be separated from the reaction mixture by centrigugation or filtration and unreacted antibody may be recovered from the supernate. The beads are washed with a chaotropic agent, such as urea, guanidine or thiocyanate, to remove adsorbed antibody and any endogenous substrate bound to the antibodies. The resulting beads are thoroughly washed to remove salts and may be stored in buffered suspensions containing bacteriostatic agents or may be lyophilized without loss of antibody activity.

HYDROLYSIS OF POLYACRYLAMIDE BEADS 100 grams of polyacrylamide beads (1-5 microns diameter) are suspended in 10 liters of 2N NaOH and stirred at room temperature (for 16 to 20 hours). The reaction mixture is neutralized with concentrated phosphoric acid (pH 6 to 7). The beads are isolated by centrifugation or filtration and washed 3 times with 10 liters of water. The washed beads are resuspended in 10 liters of 0.05 M $PO_4$ buffer and the pH adjusted to 5.5. The working bead concentration is 10 mg/ml (dry weight).

COUPLING OF ANTISERUM OF HYDROLYZED BEADS

Ten grams of hydrolyzed bead suspension (1 liter) is cooled to 4° C. and stirred magnetically. Two grams of dry EDAC, 1-Ethyl-3- (3-Dimethylaminopropyl)-carbodiimide-HCl, are added to the bead suspension. The pH of the mixture rises rapidly and then gradually declines to its original value. When the pH has dropped approximately one-half of the initial rise (pH 5.8), the antiserum or purified antibody is added to the mixture. The amount of antiserum added will vary as a function of the antibody titer, but is typically one ml. of whole antiserum per gram of beads, or less. The reaction mixture is allowed to stand at 4° C. overnite. The beads are separated and resuspended in 1L of 3M $NH_4SCN$ in PBS (phosphate buffered saline). This is allowed to stand for 1 to 2 hours and the beads are separated, washed 4 times with 1L of PBS, resuspended in PBS and allowed to stand at 4° C. overnite.

The beads may be conveniently stored at 4° in PBS for several months. Sodium Azide (0.01%) is a satisfactory preservative. Alternatively the beads may be resuspended in another buffer (e.g. barbital) and lyophilized.

PRETITRATION OF THE ANTIBODY BEADS

Suspensions of antibody beads are prepared in amounts of 2 to 20 mg/ml at regular intervals. These beads are tested in the normal assay system and the concentration of beads which gives a desired dose response and trace binding are selected by the following criteria:

The trace binding should be between 20-80%; preferably in the range of 50-60%, with a dose response such that the 5 $\mu$g/dl standard has 30-70% of the counts of the zero standard, conveniently 50%.

STANDARDS

The standards are prepared by adding spectroscopically quantitated thyroxine to thyroxine-free human serum to level of 20 $\mu$g/dl. The material thus obtained is serially diluted with thyroxine-free serum to give the other concentrations; i.e. 10, 5, 2.5 and 1 $\mu$g/dl, respectively.

TRACER/BLOCKING AGENT

The tracer/blocking agent is prepared by dissolving carrier-free $I^{125}$ thyroxine (approximately specific activity 2200 curies per millimole) and 1,8-anilinonapthalene sulfonic acid (ANS) in 0.0375 m barbital buffer, and dispensing the mixture in vials in an amount such that each vial contains 1.65 mg ANS and between 5 and 10 microcuries of $I^{125}$, such quantity being sufficient for 110 assay tubes.

The tracer/blocking agent may employ any of the blocking agents known in the art such as those disclosed in the above cited Chopra patent. In the present invention the radioactive tracer and blocking agent is precombined prior to mixing with the serum sample to be tested. This precombination is capable of being lyophilized and is highly stable, being limited only to the isotopic half life of the tracer. This precombination may be diluted with buffer before being mixed with the serum sample and in this precombined form obviates multiple sequential additions to the sample in the assay.

PREPARATION OF DYED BEADS

The preferred method for preparing dyed beads is as follows:

The dye (Alcian blue and/or yellow) in the amount of 0.25 to 1.5 g of dye per 100 g of beads (preferably of 1g/100g beads), is dissolved in a minimum quantity of 3% acetic acid (approximately) 100 ml/g.) This solution is filtered and mixed with an aqueous suspension of hydrolyzed beads at room temperature. The dye is adsorbed by the beads within one hour. Any dye which is not adsorbed can be removed by centrifugation of the beads. These dyed beads may be used as a diluent for the antibody beads, prepared as previously described. The diluent is added to titered beads to bring the total quantity of beads per assay to within a range, conveniently, of 0.5 to 2.5 mg per assay, preferably 1.5. Other quantities may be used. If the antibody bead titer is such that it is not necessary to add diluent beads, then a portion of the antibody beads themselves may be dyed in the above manner.

The following example will illustrate the assay in practice:

PROCEDURE STEPS

1. Label two 12 × 75 mm reaction tube for each standard, including the Zero, each control and each sample.
2. Add 25 μl of each standard, control, or patient sample to the appropriate tubes.
3. Add 2.0 ml of Tracer/Blocking Agent Solution to all tubes (standards, controls and samples).
4. Prepare a total counts tube by adding 2.0 ml of Tracer/Blocking Agent Solution to a 12 × 75 mm reaction tube. Set aside until Step 9.
5. Add 100 μl of the T-4 Antibody-beads to each tube. Mix each tube.
6. Allow all tubes to incubate at room temperature for at least one hour.
7. Centrifuge all tubes 10 minutes at 3000 rpm to pack the T-4 Antibody-beads on the bottom of the tube. Proceed immediately to the next step.
8. Discard the supernatants by smoothly inverting the tubes into a convenient container as they are removed from the centrifuge. Remove the last drop by gently blotting the tube rim on a paper towel.
9. Count each tube for one minute, including the total counts tube, and record the counts.

The following table summarizes samples and standards used and data obtained with the above procedure:

| Tube | CPM Minus Background | Average CPM | %B/B$_o$ | T-4 μg/dl |
|---|---|---|---|---|
| Total | 68,604 68,773 | 68,668 | — | — |
| Zero Standard | 39,826 40,254 | 40,040 | 100 | — |
| 1.0* Standard | 32,902 33,514 | 33,208 | 82.9 | — |
| 2.5* Standard | 25,944 26,362 | 26,153 | 65.3 | — |
| 5.0* Standard | 19,076 19,651 | 19,363 | 48.3 | — |
| 10.0* Standard | 13,117 12,978 | 13,047 | 32.6 | — |
| 20.0* Standard | 8,466 8,662 | 8,564 | 21.4 | — |
| Sample No. 1 | 16,912 10,804 | 16,755 | 41.8 | 6.7 |
| Sample No. 2 | 10,510 10,804 | 10,657 | 26.6 | 14.3 |

*μg/dl

Calculation of the percent of bound labeled T-4(B) associated with each of the standards and samples is done by dividing the average of the counts per minute (CPM) of each of the standards and samples by the average of the CPM of the Zero Standard ($B_o$) and multiplying the quotient by 100 to obtain %B/$B_o$.

A plot of the calculated %B/$B_o$ or the average count per minute, of each of the standards was made on the linear axis against the concentration of T-4 on the log axis of two cycle semilogarithmic paper. The results are illustrated in FIG. 1.

The following data obtained from the practice of the above procedure demonstrates the satisfactory performance of the assay:

PRECISION

Replicates of hypothyroid, euthyroid and hyperthyroid sera, assayed in a single run, yielded the following precision data:

| Serum Sample | Number of Replicates | Mean T-4 μg/dl | Standard Deviation |
|---|---|---|---|
| 1 | 16 | 2.03 | 0.09 |
| 2 | 14 | 7.15 | 0.18 |
| 3 | 15 | 12.19 | 0.57 |

Replicates of hypothyroid, euthyroid and hyperthyroid control sera, assayed by 11 different laboratories in 18 separate assays, yielded the following precision data:

| Control Serum | Number of Replicates | Mean T-4 μg/dl | Standard Deviation |
|---|---|---|---|
| 1 | 18 | 0.08 | 0.21 |
| 2 | 18 | 6.27 | 0.67 |
| 3 | 18 | 15.5 | 1.4 |

RECOVERY

Sixteen aliquots of a hypothyroid pooled serum were spiked with 5.0 and 10.0 μg/dl thyroxine and assayed in a single test run. The results are summarized below:

| Exogenous T-4 added μg/dl | Mean T-4 Measured μg/dl | Mean T-4 Recovered μg/dl | Mean Percent Recovery |
|---|---|---|---|
| 0 | 2.03 | — | — |
| 5 | 7.15 | 5.12 | 102.4 |
| 10 | 12.19 | 10.16 | 101.6 |

The above embodiment illustrates the assay for thyroxine. In order to utilize the procedure in an assay for triiodothyronine it is simply a matter of substituting appropriate antibodies for bonding to the hydrolyzed polyacrylamide and appropriate radio tracer.

What is claimed is:

1. An improved radioimmunoassay for a thyroid hormone selected from the group consisting of thyroxine and triiodothyronine in an aqueous sample, which comprises contacting hydrolyzed cross-linked polyacrylamide particles, of about 0.1–10 microns in size in the unhydrolyzed form, said particles forming a substantially stable homogeneous hydrophylic suspension with said aqueous sample through the assay, said particles having bonded thereto, by covalent bonds, antibodies against the said thyroid hormone member to be determined, the aqueous sample containing said member and a corresponding thyroid hormone member labeled with a radioactive isotope to bind part of said labeled member and unlabeled member to said antibody to produce a two phase system comprising a solid phase containing said bound part of labeled member and unlabeled member and a liquid phase containing unbound labeled member and unlabeled member, separating the two phases from each other, and measuring the radioactivity of at least one of said solid and liquid phases, the value of said radioactivity being a function of the concentration of the said member in the aqueous sample.

2. The improved method in accordance with claim 1 wherein the radioactivity of the separated solid phase is measured and the measurement is directly made following separation in the absence of any initial washings.

3. In a radioimmunoassay for the determination of a thyroid hormone selected from the group consisting of thyroxine and triiodothyronine in an aqueous serum sample, said method comprising mixing together with said aqueous serum sample containing said member to be determined, a corresponding thyroid hormone member labeled with a radioactive isotope, a blocking agent in an amount sufficient to displace essentially all of the selected thyroid hormone to be measured, and antibody in sufficient quantity and type to competitively bind the hormone to be measured, separating said hormone antibody complex from free radioactive thyroid hormone and measuring the radioactivity of the hormone antibody complex, the improvement wherein said antibodies are covalently bonded to hydrolyzed cross-linked polyacrylamide particles of about 1-5 microns in size in the unhydrolyzed form to form an antibody-polymer solid phase which forms a substantially stable homogeneous hydrophylic suspension with said aqueous sample through the assay.

4. An improved method for the determination of a thyroid hormone selected from the group consisting of thyroxine and triiodothyronine in an unextracted serum sample, which comprises mixing together with a measured amount of unextracted serum, a blocking agent in an amount sufficient to displace essentially all of the thyroid hormone to be measured, radioactively labeled thyroid hormone, of the type to be measured, and hydrolyzed polyacrylamide particles to which have been bonded, by covalent bonds, antibodies of the type to bind the hormone to measured, said polyacrylamide particles being of a size which forms a substantially stable homogeneous hydrophilic suspension with the sample solution through the assay, incubating to allow displacement of the hormone to be measured by the displacing agent and competitive binding of the labeled and unlabeled hormone to the antibodies on the basis of their relative concentration so as to produce a two-phase system including a solid phase comprising said bound portion of labeled and unlabeled hormone and a liquid phase comprising unbound labeled and unlabeled hormone, separating the two phases from each other and measuring the radioactivity of at least one of the said solid and said liquid phases, the value of said radioactivity being each a function of the concentration of said hormone in the serum sample.

5. An improved method in accordance with claim 4, wherein the determination is affected quantitatively by comparing the measured value of the radioactivity with a standard curve.

6. The improved method in accordance with claim 4, wherein said blocking agent is 8-anilino-1-naphthalene sulfonic acid (ANS).

7. The improved method in accordance with claim 4, wherein said solid phase is separated from said liquid phase by centrifugation or filtration.

8. The improved method in accordance with claim 4, wherein said thyroid hormone to be measured is thyroxine (T-4), said blocking agent is 8-anilino-1-naphthalene sulfonic acid (ANS), and said separation of the solid phase is by centrifugation or filtration.

9. The improved method in accordance with claim 4, wherein said thyroid hormone to be measured is triiodothyronine (T-3), said blocking agent is 8-anilino-1-naphthalene sulfonic acid (ANS), and said separation of the solid phase is by centrifugation or filtration.

10. The improved method in accordance with claim 4 wherein said polyacrylamide particles are present in an amount of about 0.5-2.5 mg. for each serum sample assayed.

11. The improved method in accordance with claim 4 wherein said polyacrylamide particles are a combination of particles bonded with antibodies and particles free of antibodies, the proportion of each being sufficient to produce a trace binding of about 20-80%.

12. The improved method in accordance with claim 11 wherein the proportion of said particles is selected to produce a trace binding of about 50-60%.

13. The improved method in accordance with claim 11 wherein at least some of said polyacrylamide particles free of antibodies have physically adsorbed thereon at least one dye selected from Alcian blue and Alcian yellow, said dye remaining on said particles through said assay.

14. The improved method in accordance with claim 4 wherein said incubation is executed at a temperature of about 37°-50° C to shorten the incubation period.

15. The improved method in accordance with claim 4 wherein said blocking agent and radioactively labeled hormone are precombined prior to mixing with said serum sample.

16. The improved method in accordance with claim 15 wherein said precombined blocking agent and radioactively labeled hormone are lyophilized and diluted with buffer before mixing with said serum sample.

17. A reagent for use in an immunoassay comprising hydrolyzed cross-linked polyacrylamide particles having physically adsorbed thereon at least one dye selected from Alcian yellow and Alcian blue, said dye remaining on said particles through the immunoassay in which they are used.

18. A reagent in accordance with claim 17 wherein said dye is present in the amount of 0.25 to 1.5 g. per 100 g. of particles.

19. A reagent in accordance with claim 17 wherein said polyacrylamide particles are of a size which forms a stable hydrophyllic suspension and are in admixture with a second group of similar particles which are covalently bonded with antibodies.

* * * * *